United States Patent
Iwata et al.

(10) Patent No.: US 10,173,973 B2
(45) Date of Patent: Jan. 8, 2019

(54) ALKYLIDENE AMINOGUANIDINE AND SALT THEREOF, MODIFYING COMPOSITION, MODIFIED RUBBER FOR TIRE, RUBBER COMPOSITION FOR TIRE, AND TIRE

(71) Applicant: Mitsubishi Gas Chemical Company, Inc., Tokyo (JP)

(72) Inventors: Tomoki Iwata, Tokyo (JP); Kazuyoshi Uera, Tokyo (JP); Haruka Sakai, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 15/317,643

(22) PCT Filed: Jun. 10, 2015

(86) PCT No.: PCT/JP2015/066684
§ 371 (c)(1),
(2) Date: Dec. 9, 2016

(87) PCT Pub. No.: WO2015/190504
PCT Pub. Date: Dec. 17, 2015

(65) Prior Publication Data
US 2017/0129850 A1    May 11, 2017

(30) Foreign Application Priority Data

Jun. 10, 2014 (JP) ................. 2014-119355
Jun. 10, 2014 (JP) ................. 2014-119356
Aug. 18, 2014 (JP) ................. 2014-165912
Aug. 18, 2014 (JP) ................. 2014-165913
Feb. 13, 2015 (JP) ................. 2015-026280

(51) Int. Cl.
| | | |
|---|---|---|
| C07C 281/18 | (2006.01) | |
| B60C 1/00 | (2006.01) | |
| C08C 19/22 | (2006.01) | |
| C08K 3/00 | (2018.01) | |
| C08K 5/54 | (2006.01) | |
| C08L 15/00 | (2006.01) | |
| C08K 3/04 | (2006.01) | |
| C08K 3/36 | (2006.01) | |

(52) U.S. Cl.
CPC .............. *C07C 281/18* (2013.01); *B60C 1/00* (2013.01); *C08C 19/22* (2013.01); *C08K 3/00* (2013.01); *C08K 3/04* (2013.01); *C08K 3/36* (2013.01); *C08K 5/54* (2013.01); *C08L 15/00* (2013.01)

(58) Field of Classification Search
CPC .......... C07C 281/18; C08K 3/04; C08K 3/36; C08C 19/22
See application file for complete search history.

(56) References Cited

U.S. PATENT DOCUMENTS

| | | | |
|---|---|---|---|
| 3,673,241 A | 6/1972 | Marxer | |
| 4,044,118 A | 8/1977 | McCoy et al. | |
| 4,266,044 A | 5/1981 | Timmerman et al. | |
| 2001/0034389 A1 | 10/2001 | Vasseur | |
| 2002/0028851 A1 | 3/2002 | Bianchi et al. | |
| 2004/0214192 A1 | 10/2004 | Hashida et al. | |
| 2004/0214939 A1* | 10/2004 | Patel ............ | C08K 3/005 |
| | | | 524/440 |
| 2010/0059160 A1 | 3/2010 | Sandstrom | |
| 2010/0249336 A1 | 9/2010 | Yonemoto | |
| 2011/0201078 A1 | 8/2011 | Rasmussen et al. | |

FOREIGN PATENT DOCUMENTS

| | | | | |
|---|---|---|---|---|
| GB | 842322 A | | 7/1960 | |
| GB | 932951 A | * | 7/1963 | ........... C07C 281/18 |
| GB | 954264 A | | 4/1964 | |
| JP | S50-121175 A | | 9/1975 | |
| JP | 2005-097340 A | | 4/2005 | |
| JP | 2009-108204 A | | 5/2009 | |
| JP | 2010-209253 A | | 9/2010 | |
| JP | 2010-248334 A | | 11/2010 | |

(Continued)

OTHER PUBLICATIONS

Ganesh et al; Bioorganic & Medicinal Chemistry, 2005, vol. 13, p. 257-264.*
Prasad et al; Canadian Journal of Chemistry, 1067, vol. 45, p. 2247-2252.*
Dohi et al; Langmuir, 2007, vol. 23, p. 12344-12349.*
International Search Report dated Sep. 8, 2015 for PCT/JP2015/066684 and English translation of the same (5 pages).
"Guanijin-en (Guanidine salt)", Fine Chemical, CMC Publishing Co., Ltd., Jun. 2008, vol. 37 (6), p. 72-75 (6 pages).
Junko Naito et al., "Tainai no ko-toka tyumoku sozai no kino to Kaihatsu (Function of remarkable anti-glycation material in body and development thereof)", Fine Chemical, CMC Publishing Co., Ltd., Jun. 2012, vol. 41 (6), p. 21-26 (4 pages).

(Continued)

*Primary Examiner* — Robert S Jones
(74) *Attorney, Agent, or Firm* — Fitch, Even, Tabin & Flannery LLP

(57) ABSTRACT

Provided is a compound represented by formula (1):

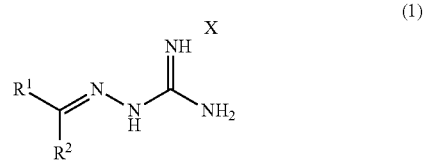

wherein X is an acid to form a salt with a guanidine site; and $R^1$ and $R^2$ are each independently any selected from the group consisting of a hydrogen atom, a $C_{1-18}$ alkyl group, a cycloalkyl group, an aryl group, an alkylaryl group, and an alkenyl group, each of the groups optionally having one or more substituents each containing a sulfur atom, a nitrogen atom, or an oxygen atom.

14 Claims, No Drawings

(56) References Cited

FOREIGN PATENT DOCUMENTS

| JP | 2011-038009 A | 2/2011 |
|---|---|---|
| JP | 2011-246513 A | 12/2011 |
| WO | 2004/003198 A1 | 1/2004 |

OTHER PUBLICATIONS

Jira, T. et al., HPLC studies on the distribution behavior of guanylic and N-phenylguanylic hydrazone derivatives, Pharmazie, 1985, 40(1), p. 34-36, p. 34, table1 (4 pages).

Baiocchi, Fred et al., Studies on Methylglyoxal bis (guanylhydrazone) analogs. II.Structural variations on methylglyoxal bis (guanylhydrazone), Journal of Medicinal Chemistry, 1963, 6(4), p. 431-435, p. 433, table 2, 1st, 2nd, 4th compounds (6 pages).

Brooks, David W. et al., Structural effects and reactivity in guanylhydrazone formation: temperature coefficients of rate of formation of several guanylhydrazones, Journal of Organic Chemistry, 1962, 27, p. 4469-4475, p. 4470, table 1, Guanylhydrazone (7 pages).

Finnegan, William G. et al., 1-(Alkylamino) guanidines, Journal of the American Chemical Society, 1952, 74, p. 2981-2983, p. 2982, table 1, Guanylhydrazone (3 pages).

Grammaticakis, P., Spectral study of nitrogen derivatives of aromatic aldehydes and ketones. IX. Benzenesulfonylhydrazones and guanylhydrazones of aldehydes, Bulletin de la Societe Chimique de France, 1952, p. 446-453, p. 453, compounds 28, 29, 32, Guanylhydrazone (9 Pages).

"HPLC studies on the distribution behavior of guanyl- and N-phenylguanylhydraz one derivatives", Jira T. et al., Pharmazie, 40(1985), H.1, pp. 34-36.

"Studies on Methylglyoxal Bis(guanylhydrazone) Analogs., II Structural Variations on Methylglyoxal Bis (guanylhydrazone)" Baiocchi Fred et al, J.Med. Chem., 6(4), Jul. 1963, pp. 431-435.

"Structural Effects and Reactivity in Guanylhydrazone Formation: Temperature Coefficients of Rate of Formation of Several Guanylydrazones", Brooks David W. et al., Org. Chem., vol. 27, Dec. 1962, pp. 4469-4475.

"1-(Alkylamino)—guanidines", Finnegan William G. et al., J,.Am. Chem., Soc., vol. 74, Jun. 20, 1952, pp. 2981-2983.

"Spectral study of nitrogen derivatives of aromatic aldehydes and ketones.IX.Benzenesul fonylhydrazones and guanylhydrazones of aldehydes" Grammatiacakis, P., Bulletin de la Societe Chimique de France, 1952, pp. 446-453.

\* cited by examiner

ALKYLIDENE AMINOGUANIDINE AND SALT THEREOF, MODIFYING COMPOSITION, MODIFIED RUBBER FOR TIRE, RUBBER COMPOSITION FOR TIRE, AND TIRE

CROSS-REFERENCE TO RELATED APPLICATIONS

This application is a U.S. national phase application filed under 35 U.S.C. § 371 of International Application PCT/JP2015/066684, filed on Jun. 10, 2015, designating the United States, which claims priority from Japanese Application Nos. 2014-119355 and 2014-119356, each filed Jun. 10, 2014, Japanese Application Nos. 2014-165912 and 2014-165913, each filed Aug. 18, 2014, and Japanese Application No. 2015-026280, filed Feb. 13, 2015, which are hereby incorporated herein by reference in their entirety.

TECHNICAL FIELD

The present invention relates to a novel alkylidene aminoguanidine and a salt thereof, a modifying composition, a modified rubber for a tire, a rubber composition for a tire, and a tire.

BACKGROUND ART

Aminoguanidine is a raw material for synthesis of medicines, dyes, photographic chemicals, gunpowder, etc., and in particular, its anti-glycation effect is widely known in the field of medicines (see Non Patent Literature 1). As the anti-glycation effect of aminoguanidine have been found inhibition of the in vitro formation of AGEs, inhibition of the crosslinking or polymerization of a protein, and prophylaxis of nephropathy, retinopathy, and neuropathy and an effect of preventing the progression of diabetes complications in an animal model of diabetes (see Non Patent Literature 2).

In addition to the above applications, aminoguanidine has been recently found to be useful for an absorber for odor components of aldehydes, i.e., an aldehyde catcher (see Patent Literature 1) and has been used as an additive for rubbers (see Patent Literature 2). More and more diverse physical properties have been required for the application, and a compound alternative to conventional aminoguanidine is required to be provided.

Fillers are additives for rubbers to be mixed in a rubber for the purpose of reinforcement or bulking of the rubber, imparting a special function to the rubber, etc. Carbon black, a representative filler, not only contributes to enhancement of the physical properties (reinforcing effect), such as elastic modulus and breaking strength, of a rubber, but also has a function of imparting conductivity, etc.

To obtain a reinforcing effect for rubbers similar to carbon black and obtain a rubber composition having low heat build-up, i.e., low loss properties, a method of using an inorganic filler such as silica is known, and has been applied, for example, to rubber compositions for environmentally friendly, fuel-efficient tires, etc.

In an inorganic filler-blended rubber composition, an inorganic filler, especially hydrophilic silica having a silanol group on the surface, blended therein agglomerates in the rubber composition due to its low affinity for a rubber, which is hydrophobic. Thus, it is required to enhance the affinity of silica for a rubber to enhance the reinforcing capability of silica and obtain an effect of lowering heat build-up. Known examples of such methods include use of a synthetic rubber the affinity of which for inorganic fillers is enhanced through end group modification with a polar group (see Patent Literature 3) and use of a synthetic rubber the affinity of which for inorganic fillers is enhanced through copolymerization of a polar group-containing monomer (see Patent Literature 4). Known examples of methods for modifying a natural rubber to introduce a polar group include a method in which a natural rubber is oxidized and then modified with a hydrazide compound having a polar group (see Patent Literature 5) and a method in which a silane coupling agent is added to a rubber composition containing a modified natural rubber having a polar group introduced and silica to further enhance the dispersibility of the silica (see Patent Literature 6).

CITATION LIST

Patent Literature

Patent Literature 1:
Japanese Patent Laid-Open No. 2005-97340
Patent Literature 2:
Japanese Patent Laid-Open No. 2010-248334
Patent Literature 3:
Japanese Patent Laid-Open No. 2010-209253
Patent Literature 4:
Japanese Patent Laid-Open No. 2011-38009
Patent Literature 5:
Japanese Patent Laid-Open No. 2009-108204
Patent Literature 6:
Japanese Patent Laid-Open No. 2011-246513

Non Patent Literature

Non Patent Literature 1:
"Guanijin-en (Guanidine salt)", Fine Chemical, CMC Publishing Co., Ltd., June 2008, Vol. 37 (6), p. 72-75
Non Patent Literature 2:
Junko Naito et al., "Tainai no ko-toka tyumoku sozai no kino to Kaihatsu (Function of remarkable anti-glycation material in body and development thereof)", Fine Chemical, CMC Publishing Co., Ltd., June 2012, Vol. 41 (6), p. 21-26

SUMMARY OF INVENTION

However, public interest in environmental issues such as the carbon dioxide concentration in the air and the air pollution is expected to increase more and more in the future, and a technique is required to provide a modified rubber, a rubber composition comprising the modified rubber and an inorganic filler such as silica and being excellent in low loss properties, and a tire each of which reduces the rolling resistance of a tire to provide fuel-efficient automobiles.

The present invention was made in view of the above circumstances, and an object of the present invention is to provide an alkylidene aminoguanidine and a salt thereof which are useful, for example, for additives for rubbers.

As a result of diligent research, the present inventors succeeded in manufacturing a novel alkylidene aminoguanidine and a salt thereof, and thus completed the present invention.

Specifically, the present invention is as follows.
<1>
A compound represented by formula (1):

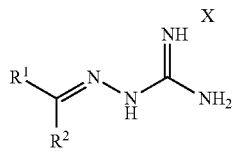
(1)

wherein X is an acid to form a salt with a guanidine site; and R¹ and R² are each independently any selected from the group consisting of a hydrogen atom, a $C_{1-18}$ alkyl group, a cycloalkyl group, an aryl group, an alkylaryl group, and an alkenyl group, each of the groups optionally having one or more substituents each containing a sulfur atom, a nitrogen atom, or an oxygen atom.
<2>
A compound represented by formula (2):

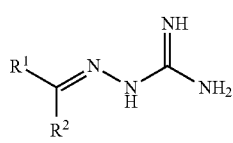
(2)

wherein R¹ and R² are each independently any selected from the group consisting of a hydrogen atom, a $C_{1-18}$ alkyl group, a cycloalkyl group, an aryl group, an alkylaryl group, and an alkenyl group, each of the groups optionally having one or more substituents each containing a sulfur atom, a nitrogen atom, or an oxygen atom.
<3>
The compound according to <1> or <2>, wherein the compound is obtained by reacting an aminoguanidine salt represented by formula (3) with a carbonyl compound represented by formula (4):

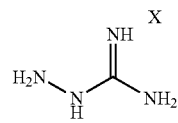
(3)

wherein X is an acid to form a salt with a guanidine site in the formula (3),

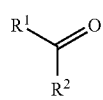
(4)

wherein R¹ and R² are each independently any selected from the group consisting of a hydrogen atom, a $C_{1-18}$ alkyl group, a cycloalkyl group, an aryl group, an alkylaryl group, and an alkenyl group, each of the groups optionally having one or more substituents each containing a sulfur atom, a nitrogen atom, or an oxygen atom.

<4>
The compound according to <1> or <2>, wherein R¹ and R² in the formula (1) or (2) are each independently any selected from the group consisting of a $C_{1-5}$ alkyl group and a hydrogen atom.
<5>
The compound according to any one of <1> to <4>, wherein the compound has a melting point of 50 to 150° C.
<6>
The compound according to <1>, which is represented by any of formulas (5) to (13):

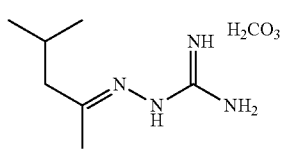
(5)

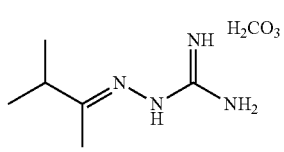
(6)

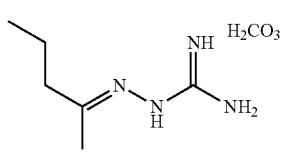
(7)

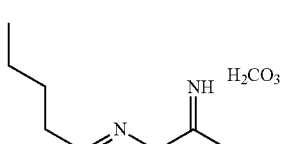
(8)

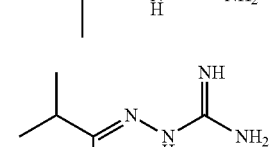
(9)

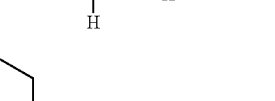
(10)

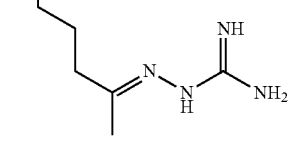
(11)

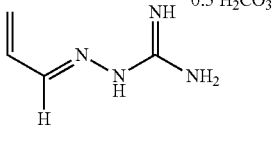
(12)

-continued

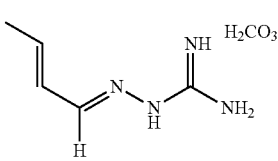

(13)

<7>
A modifying composition comprising the compound according to any one of <1> to <6>.
<8>
A modified rubber for a tire (A), which is obtained by modifying a natural rubber and/or a synthetic rubber with the compound according to any one of <1> to <6>.
<9>
The modified rubber for the tire (A) according to <8>, which is obtained by mixing the natural rubber and/or the synthetic rubber with the compound represented by the formula (1) or the formula (2) to modify the resulting mixture in a range of 20 to 180° C.
<10>
The modified rubber for the tire (A) according to <8> or <9>, wherein the compound represented by formula (1) or formula (2) is used at 0.01 to 10% by mass, based on an amount of the natural rubber and/or the synthetic rubber.
<11>
A rubber composition for a tire comprising: the modified rubber for the tire (A) according to any one of <8> to <10>; a filler comprising an inorganic filler (B); and a silane coupling agent (C).
<12>
The rubber composition for the tire according to <11>, wherein the inorganic filler (B) is silica.
<13>
The rubber composition for the tire according to <11> or <12>, wherein the filler comprises carbon black.
<14>
The rubber composition for the tire according to any one of <11> to <13> comprising the modified rubber for a tire (A), wherein the rubber composition is obtained by mixing the compound represented by the formula (1) or the formula (2), a natural rubber and/or a synthetic rubber, a filler containing an inorganic filler (B), and a silane coupling agent (C) together.
<15>
The rubber composition for the tire according to <14>, wherein a temperature in mixing is in a range of 20 to 180° C.
<16>
The rubber composition for the tire according to <14> or <15>, wherein a content of the compound represented by the formula (1) or the formula (2) is 0.01 to 10% by mass, based on an amount of the natural rubber and/or the synthetic rubber.
<17>
A tire for use in a tread of tire member, comprising the rubber composition for the tire according to any one of <11> to <16>.

The alkylidene aminoguanidine and a salt thereof according to the present invention are useful, for example, for additives for rubbers.

DESCRIPTION OF EMBODIMENTS

Hereinafter, modes for carrying out the present invention (hereinafter, simply referred to as "one embodiment(s) of the present invention" or "the present embodiment(s)") will be described in detail. The embodiments of the present invention in the following are examples for describing the present invention, and it is not intended to limit the present invention to the following description. Appropriate modifications may be made in the practice of the present invention within the gist of the present invention.

<Alkylidene Aminoguanidine and Salt, Etc., Thereof>

A compound according to one embodiment of the present invention is a compound represented by formula (1) or formula (2).

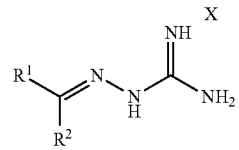

(1)

Wherein X is an acid to form a salt with a guanidine site; and $R^1$ and $R^2$ are each independently any selected from the group consisting of a hydrogen atom, a $C_{1-18}$ alkyl group, a cycloalkyl group, an aryl group, an alkylaryl group, and an alkenyl group, each of the groups optionally having one or more substituents each containing a sulfur atom, a nitrogen atom, or an oxygen atom.

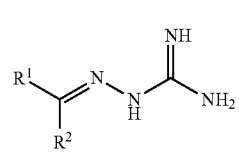

(2)

Wherein $R^1$ and $R^2$ are each independently any selected from the group consisting of a hydrogen atom, a $C_{1-18}$ alkyl group, a cycloalkyl group, an aryl group, an alkylaryl group, and an alkenyl group, each of the groups optionally having one or more substituents each containing a sulfur atom, a nitrogen atom, or an oxygen atom.

Examples of X in the formula (1) include hydrochloric acid, sulfuric acid, carbonic acid, nitric acid, acetic acid, oxalic acid, phosphoric acid, hydrobromic acid, hydroiodic acid, sulfamic acid, perchloric acid, silicic acid, boric acid, and phenylphosphinic acid. Among them, hydrochloric acid, sulfuric acid, carbonic acid, and nitric acid are preferred because of commercial availability of a guanidine salt of a raw material compound, and carbonic acid is more preferred because of ease of purification in manufacturing.

$R^1$ and $R^2$ are each independently any selected from the group consisting of a hydrogen atom, a $C_{1-18}$ alkyl group, a cycloalkyl group, an aryl group, an alkylaryl group, and an alkenyl group, each of the groups optionally having one or more substituents each containing a sulfur atom, a nitrogen atom, or an oxygen atom. Among them, $R^1$ and $R^2$ are preferably each independently a hydrogen atom or a $C_{1-5}$ alkyl group or an alkenyl group, more preferably a $C_{1-5}$ alkyl group or a hydrogen atom, and even more preferably a hydrogen atom or a $C_{1-4}$ alkyl group. The upper limit of the number of carbon atoms in each of $R^1$ and $R^2$ is preferably 4 or smaller, and more preferably 3 or smaller, which provides a better effect in an application of modification to be described later. Specific examples of such substituents include a methyl group, an ethyl group, a propyl group, an isopropyl group, a butyl group, an isobutyl group, a sec-butyl group, a tert-butyl group, a pentyl group, a 1-methylbutyl group, a 2-methylbutyl group, a 3-methylbutyl group, a 1-ethylpropyl group, a 2-ethylpropyl group, a 1,1-dimethylpropyl group, a 1,2-dimethylpropyl group, a 2,2-dimethylpropyl group, a vinyl group, a 1-methylvinyl group, a 1-ethylvinyl group, a 1-propylvinyl group, a 2-methylvinyl group, a 2-ethylvinyl group, and a 2-propylvinyl group. Among them, preferred are a methyl group, an ethyl group, a propyl group, an isopropyl group, a butyl group, an isobutyl group, a sec-butyl group, a tert-butyl group, a 1-methylbutyl group, a 2-methylbutyl group, a 3-methylbutyl group, a vinyl group, a 1-methylvinyl group, a 1-ethylvinyl group, a 2-methylvinyl group, a 2-ethylvinyl group, etc., and more preferred are a methyl group, an ethyl group, a propyl group, an isopropyl group, a n-butyl group, an isobutyl group, a sec-butyl group, a tert-butyl group, a vinyl group, a 1-methylvinyl group, a 1-ethylvinyl group, a 2-methylvinyl group, and a 2-ethylvinyl group.

Specific examples of the compound represented by the formula (1) or the formula (2) in the present embodiment include ethylideneaminoguanidine (salt), propylideneaminoguanidine (salt), butylideneaminoguanidine (salt), 3-methylbutylideneaminoguanidine (salt), 1-methylethylideneaminoguanidine (salt), 1-methylpropylideneaminoguanidine (salt), 1-methylbutylideneaminoguanidine (salt), 1-ethylpropylideneaminoguanidine (salt), 1-isopropyl-2-methylpropylideneaminoguanidine (salt), pentylideneaminoguanidine (salt), 1,3-dimethylbutylideneaminoguanidine (salt), 1,2-dimethylpropylideneaminoguanidine (salt), 1-methylbutylideneaminoguanidine (salt), 1-methylpentylideneaminoguanidine (salt), 2-methylpropylideneaminoguanidine (salt), 1-methylhexylideneaminoguanidine (salt), allylideneaminoguanidine (salt), 2-methylallylideneaminoguanidine (salt), 2-butenylideneaminoguanidine (salt), 2,6-dimethyl-4-heptylideneaminoguanidine (salt), 2-furylmethylideneaminoguanidine (salt), benzylideneaminoguanidine (salt), 4-dimethylaminophenylmethyleneaminoguanidine (salt), 4-methoxyphenylmethyleneaminoguanidine (salt), 4-hydroxyphenylmethyleneaminoguanidine (salt), 1-phenylethylideneaminoguanidine (salt), 1-methyl-3-phenylallylideneaminoguanidine (salt), diphenylmethyleneaminoguanidine (salt), and 1-(2,4-dihydroxyphenyl)benzylideneaminoguanidine (salt). Among them, examples of preferred compounds are those represented by the following formulas.

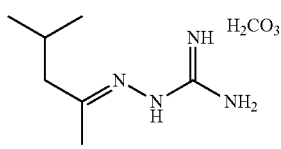

(5)

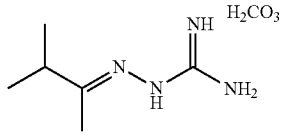

(6)

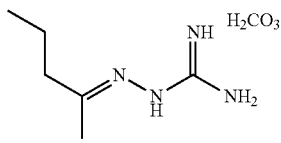

(7)

-continued

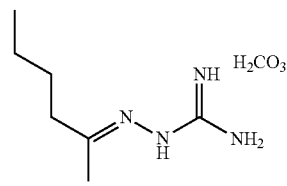

(8)

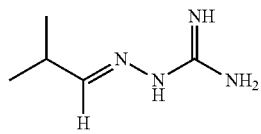

(9)

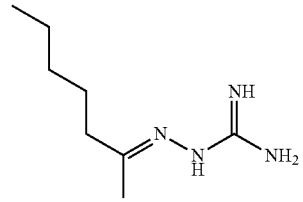

(10)

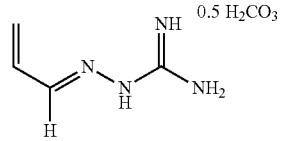

(11)

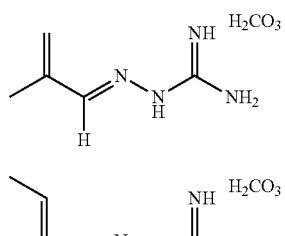

(12)

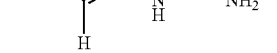

(13)

The compound represented by the formula (1) or the formula (2) in the present embodiment can be obtained by using a known method, and, for example, can be obtained by reacting an aminoguanidine salt represented by formula (3) with a carbonyl compound represented by formula (4). An aminoguanidine salt as a raw material is highly basic because the positive charge of the conjugate acid is resonance-stabilized by a plurality of nitrogen atoms present in the molecule, and thus is often present as a complex (salt) with an acid in common cases. The compound represented by the formula (1) or the formula (2) can be easily synthesized by reacting an aminoguanidine salt as a raw material with acetone, methyl isobutyl ketone, or the like, which forms an alkylidene skeleton, in water or an alcohol solvent such as methanol with an acid added thereto, if necessary. In most cases, the alkylidene aminoguanidine to be obtained forms a salt with an acid. However, an alkylidene aminoguanidine not forming a salt may be obtained contrary to the expectation. In the case that a salt is formed, an acid to form a salt with an alkylidene-substituted aminoguanidine can be appropriately selected in accordance with the types of an aminoguanidine salt as a raw material and an acid to be added. Such a manufacturing method is preferred from the viewpoint of manufacturing cost.

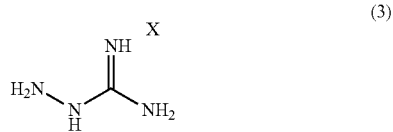

(3)

Wherein X is an acid to form a salt with a guanidine site.

(4)

Wherein $R^1$ and $R^2$ are each independently any selected from the group consisting of a hydrogen atom, a $C_{1-18}$ alkyl group, a cycloalkyl group, an aryl group, an alkylaryl group, and an alkenyl group, each of the groups optionally having one or more substituents each containing a sulfur atom, a nitrogen atom, or an oxygen atom.

X in formula (3) can be an acid capable of forming a salt with a guanidine site, and the type of the acid is not limited. Examples thereof include organic acids (acetic acid, oxalic acid, p-toluenesulfonic acid, etc.) and inorganic acids (hydrochloric acid, hydrobromic acid, hydroiodic acid, nitric acid, sulfuric acid, phosphoric acid, carbonic acid, sulfamic acid, perchloric acid, silicic acid, boric acid, phenylphosphinic acid, etc.).

Specific examples of the compound represented by the formula (3) include aminoguanidine carbonate (melting point: 162° C. (decomposition)), aminoguanidine hydrochloride (melting point: 165° C.), aminoguanidine hydroiodide (melting point: 115 to 118° C.), aminoguanidine hemisulfate (melting point: 207° C.), aminoguanidine nitrate (melting point: 145 to 147° C.), aminoguanidine oxalate (melting point: 209° C.), aminoguanidine phosphate (melting point: 144° C.), aminoguanidine acetate, aminoguanidine sulfamate, and aminoguanidine perchlorate. Among them, preferred are aminoguanidine carbonate, aminoguanidine hydrochloride, aminoguanidine hemisulfate, and aminoguanidine nitrate because of commercial availability.

Specific examples of the compound represented by the formula (4) include methyl isopropyl ketone, 2-pentanone, 2-hexanone, isobutyraldehyde, 2-heptanone, methyl isobutyl ketone, acrolein, methacrolein, and crotonaldehyde. Among them, methyl isobutyl ketone is preferably used from the viewpoint of commercial availability. These carbonyl compounds are all a known compound, and available as a commercial product.

Next, reaction conditions for the compound represented by the formula (3) and the compound represented by the formula (4) will be described in detail. To allow the reaction to proceed, 1 mol to an excessive amount of the carbonyl compound represented by the formula (4) and, as necessary, 0.001 to 1 mol of an acid catalyst as a condensation promoter, per mole of the compound represented by the formula (3), are stirred in a polar solvent such as water and an alcohol under normal pressure at 0 to 100° C. for about 10 minutes to 24 hours. After the reaction, the target product is purified by using a known method. Examples of such methods include a method in which a crystal is precipitated through cooling with ice water or the like and isolated to afford a crude crystal.

The use ratio of the aminoguanidine salt to the carbonyl compound is 1:1 to 1:100, and preferably 1:1 to 1:10 in a mole ratio. The reaction may be performed at room temperature, or under heating, as necessary, and is performed preferably at 0 to 100° C., more preferably at about 20 to 80° C., in view of the boiling point of the carbonyl compound as a raw material.

Examples of the above polar solvent include water, methanol, ethanol, propanol, isopropyl alcohol, butanol, and isobutyl alcohol. Alternatively, the carbonyl compound as a raw material, that is, 3-methyl-2-butanone, 2-pentanone, 2-hexanone, 2-heptanone, 4-methyl-2-pentanone (methyl isobutyl ketone), isobutyraldehyde, 2,4-dimethyl-3-pentanone, or the like, may be used as a solvent.

Examples of the above condensation promoter include hydrochloric acid, sulfuric acid, acetic acid, p-toluenesulfonic acid, nitric acid, oxalic acid, phosphoric acid, hydrobromic acid, hydroiodic acid, sulfamic acid, and perchloric acid. It is preferred to use an acid identical to the acid of the guanidine salt as a raw material.

In the case that a crystal is precipitated through a cooling operation or the like after the completion of the reaction, the resultant crystal is separated by filtration and washed with water, an alcohol, or the like, and then dried under reduced pressure to afford the compound according to the present embodiment.

In the case that a homogeneous solution is formed with no crystal precipitated after the reaction, a crystal can be precipitated by using, for example the following method. To the homogeneous reaction solution, a weakly basic aqueous solution containing a carbonate such as an aqueous solution of sodium carbonate and an aqueous solution of sodium hydrogen carbonate is added to precipitate a crystal of an alkylidene aminoguanidine or a carbonate thereof. The crystal is separated by filtration and subjected to the above operations to afford the compound according to the present embodiment.

In most cases, the product to be obtained by the operation of adding the aqueous solution containing a carbonate forms a salt with carbonic acid. However, depending on the type of the carbonyl compound used, a hemicarbonate or an alkylidene aminoguanidine not forming a salt may be obtained contrary to the expectation. Examples of carbonyl compounds which provide a hemicarbonate include acrolein. Examples of carbonyl compounds which provide an alkylidene aminoguanidine not forming a salt include isobutyraldehyde, 2-heptanone, and cinnamaldehyde. Examples of carbonyl compounds which provide an alkylidene aminoguanidine carbonate include methyl isobutyl ketone, methyl isopropyl ketone, 2-pentanone, 2-hexanone, acetophenone, and benzalacetone.

The alkylidene aminoguanidine skeleton of the compound according to the present embodiment represented by the formula (1) or the formula (2) can be identified through $^1$H-NMR, and the salt formed with an acid can be identified through elemental analysis.

In the case of use for an additive for rubbers, the melting point of the compound according to the present embodiment represented by the formula (1) or the formula (2) is preferably 50 to 150° C. from the viewpoint of enhancement of the low loss properties and breaking strength of a vulcanized rubber composition containing an inorganic filler such as silica. If the melting point is 50 to 150° C., the compound is solid at normal temperature and thus good workability is provided, and in addition the compound melts at a kneading temperature and vulcanizing temperature for a rubber and mixing with a rubber is thus facilitated.

<Modifying Composition, Modified Rubber for Tire, Rubber Composition for Tire, Tire, Etc.>

The compound represented by the formula (1) or the formula (2) can be at least suitably used as a modifier to produce a modified rubber or the like. Specifically, a modifying composition according to one embodiment of the present invention can be obtained by blending the compound represented by the formula (1) or the formula (2). In the modifying composition, an additional component to be described later may be appropriately blended, as necessary. The modifying composition according to the present embodiment can effectively enhance physical properties desired for a modified rubber to be used especially for a tire member (low loss properties, breaking strength, etc.).

A modified rubber for a tire (A) according to one embodiment of the present invention (hereinafter, occasionally referred to as "modified rubber (A)" simply) can be obtained by modifying a natural rubber and/or a synthetic rubber with the compound represented by the formula (1) or the formula (2). Use of the modified rubber (A) for a member of a tire or the like provides an excellent effect on low loss properties, breaking strength, etc. Now, modification for the modified rubber (A), etc., will be described. However, modification of a natural rubber or synthetic rubber with the above-mentioned modifying composition also provides the same effect and provides the same modified rubber (A) unless otherwise stated.

For a raw material rubber of the modified rubber (A) according to the present embodiment, a natural rubber, a synthetic rubber, or both of them may be used. In particular, a natural rubber is suitable because use of it provides the advantageous effect of the present embodiment significantly. The reason is that, in contrast to synthetic rubbers, into which a polar group can be introduced in polymerization in a simple manner, for example, as in the case of a synthetic rubber whose affinity for inorganic fillers has been enhanced through end modification with a polar group described in Patent Literature 1, a synthetic rubber whose affinity for inorganic fillers has been enhanced through copolymerization of a polar group-containing monomer described in Patent Literature 2, etc., natural rubbers cannot be applied with such approaches.

For the natural rubber, a sheet rubber or a block rubber each obtained by coagulating and drying a natural rubber latex may be used as a raw material. Examples of sheet rubbers include, in accordance with the classification of "International Standards of Quality and Packing for Natural Rubber Grades" (commonly called "Green Book"), ribbed smoked sheets (RSS), which are obtained by smoking a sheet to dry, air-dried sheets (ADS), which are obtained by drying a sheet with hot air, and crepes, which are obtained by sufficiently washing a coagulate with water followed by drying with hot air, and further include TC rubbers (Technically Classified Rubber), SP rubbers (Super Processing Rubber), MG rubbers, PP crepes, softeners, and peptizer-containing rubbers. Examples of block rubbers include SMR (Standard Malaysian Rubber) from Malaysia, SIR from Indonesia, TTR from Thailand, SCR from Sri Lanka, and SSR from Singapore. One of these natural rubber raw materials may be used singly, or two or more thereof may be used in combination.

Alternatively, a rubber obtained by coagulating a natural rubber latex after oxidation treatment may be used, and oxidation of a natural rubber latex can be performed by using a known method. For example, oxidation of a natural rubber latex can be performed by air-oxidizing a natural rubber latex dissolved in an organic solvent at a fraction of 1 to 30% by mass in the presence of a metal oxidation catalyst in accordance with Japanese Patent Laid-Open No. 8-81505. As described in Japanese Patent Laid-Open No. 9-136903, for example, oxidation can be performed by adding a carbonyl compound to a natural rubber latex. In the case that air oxidation is performed as an oxidizing method, air oxidation may be performed in the presence of a radical generator to promote air oxidation as described in Japanese Patent Laid-Open No. 9-136903. For example, a peroxide radical generator, a redox-type radical generator, an azo radical generator, or the like is suitably used for the radical generator.

Examples of synthetic rubbers which can be used for a raw material of the modified rubber (A) include diene rubbers having a double bond in the molecule such as 1,4-polybutadiene, 1,2-polybutadiene, 1,4-polyisoprene, 3,4-polyisoprene, styrene-butadiene rubbers, end-modified styrene-butadiene rubbers, chloroprene rubbers, nitrile rubbers, ethylene-propylene rubbers, ethylene-propylene-diene rubbers.

In the present embodiment, the above-described natural rubber, modified rubber, or both of them may be used. In other words, one of them may be used singly, or two or more thereof may be used in combination.

A rubber modifier according to one embodiment of the present invention is any of the alkylidene aminoguanidine salt and alkylidene aminoguanidine represented by the formula (1) and the formula (2), respectively.

A modified rubber obtained by reacting the modifier with a rubber has a polar group such as an amino group, and thus affinity for a polar group of an inorganic filler, particularly in the case of silica, affinity for a silanol group on the surface of silica is enhanced. As a result, the adhesion between the rubber and the inorganic filler is enhanced, and a molded rubber product having excellent low loss properties is provided in manufacturing a molded rubber product such as a tire.

Next, a method for manufacturing the modified rubber according to the present embodiment will be described. The modified rubber according to the present embodiment is obtained by mixing the compound represented by the formula (1) or the formula (2) and a rubber by using a mixer, an extruder, a kneader, or the like. It is preferred to mix by using a kneader from the viewpoint of enhancement of dispersibility. For adding the compound represented by the formula (1) or the formula (2) into a mixer, an extruder, a kneader, or the like, any of a method of adding a powder of the compound directly, a method of adding a solution of the compound dissolved in a solvent, and a method of adding the compound in an emulsion solution may be used.

Although reaction conditions for obtaining the modified rubber according to the present embodiment are not limited, the reaction temperature for a rubber and the modifier is preferably 20 to 180° C., and more preferably 50 to 160° C. Controlling the reaction temperature in such a temperature range enables sufficient mixing of a rubber and the modifier and further the decomposition of the modifier can be prevented. The kneading duration for a rubber is preferably controlled to 0.5 to 30 minutes at the above reaction temperature, and is more preferably 2 to 10 minutes. A kneading duration of 0.5 to 30 minutes allows a rubber and the modifier to react sufficiently without deterioration of productivity. Regarding to the reaction atmosphere, it is preferred to perform the reaction in the presence of oxygen, for example, in air. The reason is that a part of a rubber is oxidized through kneading in the presence of oxygen and the reactivity to the modifier is enhanced.

Although the modified rubber according to the present embodiment can be obtained by mixing the modifier and a rubber at once by using an extruder, a kneader, or the like, an approach in which a rubber obtained by coagulating a natural rubber latex after oxidation treatment is used, and an approach in which a step of applying mechanical force to a raw material rubber, which is called mastication, is carried out before addition of the modifier to dissociate agglomerations (associations) of molecules and cleave the molecular chain for controlling the plasticity of the rubber to a plasticity which allows for easy processing are also preferably employed because the reactivity between the modifier and a rubber can be enhanced. In the step of mastication, a peptizer may be used.

In addition, if the modifier, a rubber, a filler containing an inorganic filler, a silane coupling agent, and compounding agents appropriately selected as necessary are blended and mixed together by using a mixer, an extruder, a kneader, or the like, a modified rubber is partly formed in the rubber composition. This approach is more preferred than the approach in which the modifier and a rubber are mixed together from the viewpoint of working efficiency. This operation provides a rubber composition according to one embodiment of the present invention.

The amount of the modifier to be used in manufacturing the modified rubber according to the present embodiment is preferably 0.01 to 10% by mass, and more preferably 0.1 to 3% by mass, based on the amount of the rubber component (natural rubber and/or synthetic rubber) because a small number of polar groups evenly introduced into each rubber molecule allow the modified rubber obtained to have an enhanced affinity for a filler such as silica and carbon black without lowering processability, and thus a rubber composition having excellent low loss properties is provided. In the case that a natural rubber and a synthetic rubber are used in combination, the amount of the compound here refers to the amount based on the total amount of the natural rubber and the synthetic rubber.

A rubber composition for a tire according to one embodiment of the present invention (hereinafter, occasionally referred to as "rubber composition" simply) comprises the modified rubber (A), a filler containing an inorganic filler (B), and a silane coupling agent (C).

The inorganic filler (B) in the present embodiment refers to an inorganic compound containing at least one selected from silicon, oxides or hydroxides of typical metals or transition metals and hydrates thereof, and carbonates of these metals.

Specifically, the inorganic filler (B) is not limited as long as it is an inorganic filler used in the art. Carbon black to be described later is not included in the inorganic filler (B) here, and does not fall under the inorganic filler (B). Inorganic fillers are roughly classified into reinforcing fillers such as silica having an active surface and surface-treated clay and non-reinforcing fillers such as calcium carbonate, clay, and talc. Specific examples of the inorganic filler (B) include silica, calcium carbonate, magnesium carbonate, aluminum oxide, aluminum hydroxide, aluminum silicate (clay), magnesium silicate (talc), calcium silicate, and zinc oxide. In view of interaction with the modified rubber, it is preferred to use any of the reinforcing fillers, and silica is more preferred among them. The silica is not limited, and wet silica (hydrated silicic acid), dry silica (silicic anhydride), or the like may be used.

In the case that silica is used, the BET specific surface area is preferably 40 to 350 $m^2/g$. If the BET specific surface area of silica is within the range, the particle diameter of the silica becomes appropriate, which leads to enhancement of the tensile strength and reduction of hysteresis loss. The BET specific surface area can be measured in accordance with JIS 28830: 2013.

In addition to the above inorganic filler (B), carbon black may be added as a filler to be used for the rubber composition according to the present embodiment to enhance the reinforcing effect. Here, carbon black is a filler different from the above inorganic filler (B), and should be clearly discriminated from the inorganic filler (B). Examples of carbon black include those of various grades GPF, FEF, SRF, HAF, ISAF, and SAF.

For the rubber composition according to the present embodiment, the modifier (compound represented by formula (1) or formula (2)), a rubber (natural rubber and/or synthetic rubber), a filler containing an inorganic filler (B), and a silane coupling agent (C) may be mixed together to produce a rubber composition containing the modified rubber (A).

The temperature in mixing is not limited, but preferably 20 to 180° C., and more preferably 50 to 160° C. Controlling the reaction temperature within the temperature range enables sufficient mixing of a rubber and the modifier and further the decomposition of the modifier can be prevented. The kneading duration for a rubber is preferably controlled to 0.5 to 30 minutes at the above reaction temperature, and is more preferably 2 to 10 minutes. A kneading duration of 0.5 to 30 minutes allows a rubber and the modifier to react sufficiently without deterioration of productivity. Regarding to the reaction atmosphere, it is preferred to perform the reaction in the presence of oxygen, for example, in air. The reason is that a part of a rubber is oxidized through kneading in the presence of oxygen and the reactivity to the modifier is enhanced.

The amount of the modifier to be used in mixing is preferably 0.01 to 10% by mass, and more preferably 0.1 to 3% by mass, based on the amount of the rubber component (natural rubber and/or synthetic rubber). In the case that a natural rubber and a synthetic rubber are used in combination, the amount of the modifier to be used refers to the amount based on the total amount of the natural rubber and the synthetic rubber.

The total content of the inorganic filler (B) and carbon black in the rubber composition according to the present embodiment is not limited, but preferably 5 to 100 parts by mass, and more preferably 20 to 80 parts by mass, based on 100 parts by mass of other organic components of the rubber composition such as the modified rubber (A) to obtain a sufficient loss-reduction effect and reinforcing effect without deterioration of processability.

The silane coupling agent (C) in the present embodiment is not limited, and examples thereof include bis-(3-triethoxysilylpropyl) tetrasulfide, bis-(3-trimethoxysilylpropyl) tetrasulfide, bis-(3-methyldimethoxysilylpropyl) tetrasulfide, bis-(2-triethoxysilylethyl) tetrasulfide, bis-(3-triethoxysilylpropyl) disulfide, bis-(3-trimethoxysilylpropyl) disulfide, bis-(3-triethoxysilylpropyl) trisulfide, 3-hexanoylthiopropyltriethoxysilane, 3-octanoylthiopropyltriethoxysilane, 3-decanoylthiopropyltriethoxysilane, 3-lauroylthiopropyltriethoxysilane, 2-hexanoylthioethyltriethoxysilane, 2-octanoylthioethyltriethoxysilane, 2-decanoylthioethyltriethoxysilane, 2-lauroylthioethyltriethoxysilane, 3-hexanoylthiopropyltrimethoxysilane, 3-octanoylthiopropyltrimethoxysilane, 3-decanoylthiopropyltrimethoxysilane, 3-lauroylthiopropyltrimethoxysilane, 2-hexanoylthioethyltrimethoxysilane, 2-octanoylthioethyltrimethoxysilane, 2-decanoylthioethyltrimethoxysilane, 2-lauroylthioethyltrimethoxysilane, 3-mercaptopropyltrimethoxysilane, 3-mercaptopropyltriethoxysilane, 3-mercaptopropylmethyldimethoxysilane, 3-aminopropyltrimethoxysilane, 3-aminopropyltriethoxysilane, γ-glycidoxypropyltrimethoxysilane, γ-glycidoxypropylmethyldiethoxysilane, 3-trimethoxysilylpropyl-N,N-dimethylthiocarbamoyl tetrasulfide, 3-trimethoxysilylpropylbenzothiazolyl tetrasulfide, and 3-trimethoxysilylpropylmethacryloyl monosulfide. The content is preferably 1 to 20 parts by mass, based on 100 parts by mass of the above inorganic filler.

In addition to the modified rubber, a rubber, and the filler containing an inorganic filler, compounding agents commonly used in the rubber industry, such as an antioxidant, a softener, a vulcanization accelerator, a vulcanization-accelerating aid, and vulcanizing agent, may be appropriately selected and blended in the rubber composition according to the present embodiment, without interfering with the object of the present embodiment. For these compounding agents, commercial products can be suitably used.

The type of the antioxidant is not limited, and examples thereof include naphthylamine antioxidants, p-phenylenediamine antioxidants, hydroquinone derivative antioxidants, bis-, tris-, and polyphenol antioxidants, diphenylamine antioxidants, quinoline antioxidants, monophenol antioxidants, thiobisphenol antioxidants, hindered phenol antioxidants, and phenol antioxidants. From the viewpoint of a higher antioxidizing effect, amine antioxidants such as p-phenylenediamine antioxidants and diphenyl amine antioxidants are preferred. Examples of diphenyl amine antioxidants include 4,4'-(α-methylbenzyl)diphenylamine, 4,4'-(α,α-dimethylbenzyl)diphenylamine, p-(p-toluenesulfonylamido)diphenylamine, and 4,4'-dioctyldiphenylamine. Among them, 4,4'-(α-methylbenzyl)diphenylamine is the most preferred from the viewpoint of an even higher antioxidizing effect. Examples of p-phenylenediamine antioxidants include N,N'-diphenyl-p-phenylenediamine, N-isopropyl-N'-phenyl-p-phenylenediamine, N,N'-di-2-naphthyl-p-phenylenediamine, N-cyclohexyl-N'-phenyl-p-phenylenediamine, N-phenyl-N'-(3-methacryloyloxy-2-hydroxypropyl)-p-phenylenediamine, N,N'-bis(1-methylheptyl)-p-phenylenediamine, N,N'-bis(1,4-dimethylpentyl)-p-phenylenediamine, N,N'-bis(1-ethyl-3-methylpentyl)-p-phenylenediamine, and N-(1,3-dimethylbutyl)-N'-phenyl-p-phenylenediamine. Among them, N-(1,3-dimethylbutyl)-N'-phenyl-p-phenylenediamine is the most preferred from the viewpoint of an even higher antioxidizing effect and cost. The content of the antioxidant in the rubber composition is preferably 0.1 to 5% by mass, based on the amount of the rubber component of the rubber composition.

The type of the softener is not limited, and examples thereof include mineral oil softeners derived from petroleum and coal tar, vegetable oil softeners derived from fatty oils and pine trees, and synthetic resin softeners.

The type of the vulcanization accelerator is not limited, and examples thereof include thiazole vulcanization accelerators such as mercaptobenzothiazole and di-2-benzothiazolyl disulfide; sulfenamide vulcanization accelerators such as N-cyclohexyl-2-benzothiazolylsulfenamide, N,N'-dicyclohexyl-2-benzothiazolylsulfenamide, and N'-tert-butyl-2-benzothiazolylsulfenamide; and guanidine vulcanization accelerators such as diphenylguanidine. One of these vulcanization accelerators may be used singly, or two or more thereof may be used in combination. The content is preferably 0.1 to 5 parts by mass, based on 100 parts by mass of the rubber component. The vulcanization-accelerating aid is not limited, and examples thereof include stearic acid and zinc oxide.

Regarding the type of the vulcanizing agent, vulcanizing agents commonly used in the art may be appropriately used, and examples thereof include sulfur and peroxides. Among them, sulfur is preferred. The content of the vulcanizing agent is preferably 0.1 to 5 parts by mass, and more preferably 0.5 to 3 parts by mass, based on 100 parts by mass of the rubber component. If the lower limit of the content of the vulcanizing agent is the above value or more, sufficient vulcanization can be achieved. If the upper limit of the content of the vulcanizing agent is the above value or less, what is called scorch time is not too shortened and failure such as burning of a rubber during kneading can be effectively prevented.

A tire according to one embodiment of the present invention is characterized by comprising the above rubber composition, and it is preferred to use the rubber composition for the tread. A tire for use in the tread, which comprises the rubber composition is excellent in fuel efficiency. The tire according to the present embodiment is not limited except that the rubber composition is used for any of the members of the tire, and can be manufactured by using a conventional method. Examples of gas to be used for filling the tire include, in addition to normal air and air having an adjusted oxygen partial pressure, inert gasses such as nitrogen, argon, and helium.

EXAMPLES

Hereinafter, the present invention will be described in more detail with reference to Examples, but the present invention is never limited to the following Examples.

Experiment A (Example A-1) Synthesis of 1,3-dimethylbutylideneaminoguanidine carbonate (5)

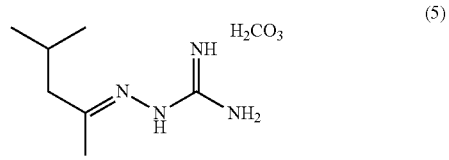

(5)

To a 50 mL eggplant flask, 1.329 g (12 mmol) of aminoguanidine hydrochloride, 6 mL of methanol, and 0.25 mL of 12 N hydrochloric acid were added and stirred at room temperature for 10 minutes, and 1.568 g (16 mmol) of methyl isobutyl ketone (MIBK) was then added thereto and the resultant was stirred with a magnetic stirrer at room temperature. After 2.5 hours of stirring, the reaction solution was added dropwise to 20 mL of a saturated aqueous solution of sodium hydrogen carbonate to precipitate a white crystal, which was collected by filtration, washed with water, and then vacuum-dried at 50° C. for 5 hours to afford 2.357 g (11 mmol) of a white solid. The solid obtained was analyzed by using $^1$H-NMR, and confirmed to be 1,3-dimethylbutylideneaminoguanidine carbonate ($^1$H-NMR (DMSO-d6, 500 MHz, δ; ppm)=0.8 (d; 6H), 1.8 (s; 3H), 1.9 (m; 1H), 2.0 (d; 2H), 5.0-5.6 (br)). The mole yield was 92%.

The melting point was measured with the micro melting point measurement apparatus BY-1 (manufactured by YAZAWA Kagaku Co., Ltd.) to be 96 to 97° C. Elemental analysis was performed with the carbon/hydrogen/nitrogen simultaneous determination apparatus CHN coder MT-6 (manufactured by YANACO Co., Ltd.), and the result was as follows. Calc.: C, 44.03; H, 8.31; N, 25.67. Found: C, 43.93; H, 8.30; N, 25.57.

(Example A-2) Synthesis of
1,2-dimethylpropylideneaminoguanidine carbonate
(6)

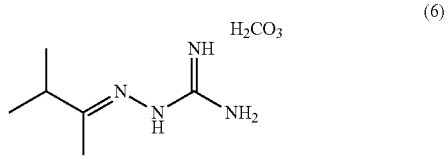

(6)

To a 50 mL eggplant flask, 1.324 g (12 mmol) of aminoguanidine hydrochloride, 6 mL of water, and 0.05 mL of 12 N hydrochloric acid were added and stirred at room temperature for 10 minutes, and 1.525 g (18 mmol) of 3-methyl-2-butanone was then added thereto and the resultant was stirred with a magnetic stirrer at room temperature. After 2.0 hours of stirring, the reaction solution was added dropwise to 20 mL of a saturated aqueous solution of sodium hydrogen carbonate to precipitate a white crystal, which was collected by filtration, washed with water, and then vacuum-dried at 50° C. for 18 hours to afford 1.802 g (8.8 mmol) of a white solid. The solid obtained was analyzed by using $^1$H-NMR, and confirmed to be 1,2-dimethylpropylideneaminoguanidine carbonate ($^1$H-NMR (DMSO-d6, 500 MHz, δ; ppm)=1.0 (d; 6H), 1.8 (s; 3H), 2.4 (m; 1H)). The mole yield was 73%. The melting point was measured with the micro melting point measurement apparatus BY-1 (manufactured by YAZAWA Kagaku Co., Ltd.) to be 104 to 105° C. Elemental analysis was performed with the carbon/hydrogen/nitrogen simultaneous determination apparatus CHN coder MT-6 (manufactured by YANACO Co., Ltd.), and the result was as follows. Calc.: C, 41.17; H, 7.90; N, 27.43. Found: C, 40.96; H, 7.88; N, 27.33.

(Example A-3) Synthesis of
1-methylbutylideneaminoguanidine carbonate (7)

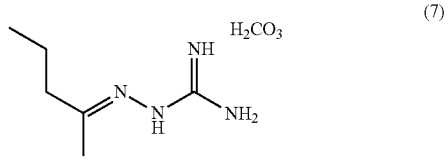

(7)

To a 50 mL eggplant flask, 1.329 g (12 mmol) of aminoguanidine hydrochloride, 6 mL of water, and 0.05 mL of 12 N hydrochloric acid were added and stirred at room temperature for 10 minutes, and 1.636 g (19 mmol) of 2-pentanone was then added thereto and the resultant was stirred with a magnetic stirrer at room temperature. After 2.0 hours of stirring, the reaction solution was added dropwise to 20 mL of a saturated aqueous solution of sodium hydrogen carbonate to precipitate a white crystal, which was collected by filtration, washed with water, and then vacuum-dried at 50° C. for 18 hours to afford 1.244 g (6.1 mmol) of a white solid. The solid obtained was analyzed by using $^1$H-NMR, and confirmed to be 1-methylbutylideneaminoguanidine carbonate ($^1$H-NMR (DMSO-d6, 500 MHz, δ; ppm)=0.9 (t; 3H), 1.5 (m; 2H), 1.8 (s; 3H), 2.1 (t; 2H)). The mole yield was 51%. The melting point was measured with the micro melting point measurement apparatus BY-1 (manufactured by YAZAWA Kagaku Co., Ltd.) to be 84 to 85° C. Elemental analysis was performed with the carbon/hydrogen/nitrogen simultaneous determination apparatus CHN coder MT-6 (manufactured by YANACO Co., Ltd.), and the result was as follows. Calc.: C, 41.17; H, 7.90; N, 27.43. Found: C, 42.59; H, 8.23; N, 29.43.

(Example A-4) Synthesis of
1-methylpentylideneaminoguanidine carbonate (8)

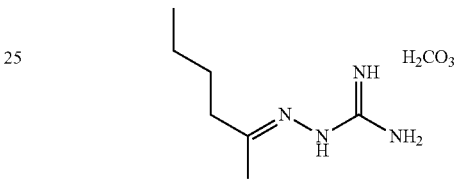

(8)

To a 50 mL eggplant flask, 1.326 g (12 mmol) of aminoguanidine hydrochloride, 6 mL of water, and 0.05 mL of 12 N hydrochloric acid were added and stirred at room temperature for 10 minutes, and 1.663 g (17 mmol) of 2-hexanone was then added thereto and the resultant was stirred with a magnetic stirrer at room temperature. After 2.0 hours of stirring, the reaction solution was added dropwise to 20 mL of a saturated aqueous solution of sodium hydrogen carbonate to precipitate a white crystal, which was collected by filtration, washed with water, and then vacuum-dried at 50° C. for 18 hours to afford 1.658 g (7.6 mmol) of a white solid. The solid obtained was analyzed by using $^1$H-NMR, and confirmed to be 1-methylpentylideneaminoguanidine carbonate ($^1$H-NMR (DMSO-d6, 500 MHz, δ; ppm)=0.9 (t; 3H), 1.3 (m; 2H), 1.4 (m; 2H), 1.8 (s; 3H), 2.1 (t; 2H), 4.9-5.5 (br)). The mole yield was 63%. The melting point was measured with the micro melting point measurement apparatus BY-1 (manufactured by YAZAWA Kagaku Co., Ltd.) to be 70 to 71° C. Elemental analysis was performed with the carbon/hydrogen/nitrogen simultaneous determination apparatus CHN coder MT-6 (manufactured by YANACO Co., Ltd.), and the result was as follows. Calc.: C, 44.03; H, 8.31; N, 25.67. Found: C, 44.24; H, 8.12; N, 27.82.

(Example A-5) Synthesis of
2-methylpropylideneaminoguanidine (9)

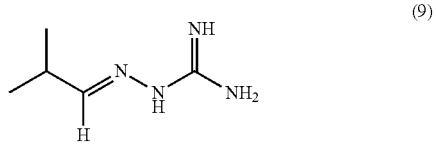

(9)

To a 50 mL eggplant flask, 1.324 g (12 mmol) of aminoguanidine hydrochloride, 6 mL of water, and 0.05 mL of 12 N hydrochloric acid were added and stirred at room temperature for 10 minutes, and 1.500 g (21 mmol) of isobutyraldehyde was then added thereto and the resultant was stirred with a magnetic stirrer at room temperature. After 2.0 hours of stirring, the reaction solution was added dropwise to 20 mL of a saturated aqueous solution of sodium hydrogen carbonate to precipitate a white crystal, which was collected by filtration, washed with water, and then vacuum-dried at 50° C. for 18 hours to afford 0.792 g (4.2 mmol) of a white solid. The solid obtained was analyzed by using $^1$H-NMR, and confirmed to be 2-methylpropylideneaminoguanidine ($^1$H-NMR (DMSO-d6, 500 MHz, δ; ppm)=1.0 (d; 6H), 2.4 (m; 1H), 4.9-5.6 (br), 7.2 (d; 1H)). The mole yield was 35%. The melting point was measured with the micro melting point measurement apparatus BY-1 (manufactured by YAZAWA Kagaku Co., Ltd.) to be 59 to 60° C. Elemental analysis was performed with the carbon/hydrogen/nitrogen simultaneous determination apparatus CHN coder MT-6 (manufactured by YANACO Co., Ltd.), and the result was as follows. Calc.: C, 46.85; H, 9.44; N, 43.71. Found: C, 45.13; H, 9.18; N, 40.89.

(Example A-6) Synthesis of 1-methylhexylideneaminoguanidine (10)

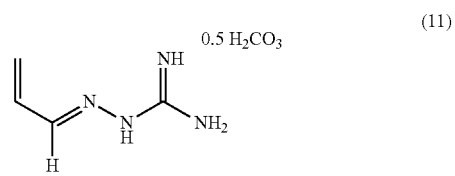

(10)

To a 50 mL eggplant flask, 1.326 g (12 mmol) of aminoguanidine hydrochloride, 6 mL of water, and 0.05 mL of 12 N hydrochloric acid were added and stirred at room temperature for 10 minutes, and 1.730 g (15 mmol) of 2-heptanone was then added thereto and the resultant was stirred with a magnetic stirrer at room temperature. After 2.0 hours of stirring, the reaction solution was added dropwise to 20 mL of a saturated aqueous solution of sodium hydrogen carbonate to precipitate a white crystal, which was collected by filtration, washed with water, and then vacuum-dried at 50° C. for 18 hours to afford 1.576 g (6.7 mmol) of a white solid. The solid obtained was analyzed by using $^1$H-NMR, and confirmed to be 1-methylhexylideneaminoguanidine ($^1$H-NMR (DMSO-d6, 500 MHz, δ; ppm)=0.9 (t; 3H), 1.3 (m; 4H), 1.5 (m; 2H), 1.8 (s; 3H), 2.1 (t; 2H), 4.9-5.5 (br)). The mole yield was 56%. The melting point was measured with the micro melting point measurement apparatus BY-1 (manufactured by YAZAWA Kagaku Co., Ltd.) to be 74 to 75° C. Elemental analysis was performed with the carbon/hydrogen/nitrogen simultaneous determination apparatus CHN coder MT-6 (manufactured by YANACO Co., Ltd.), and the result was as follows. Calc.: C, 56.44; H, 10.66; N, 32.91. Found: C, 56.01; H, 10.80; N, 32.62.

(Example A-7) Synthesis of allylideneaminoguanidine hemicarbonate (11)

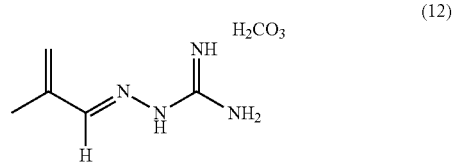

(11)

To a 50 mL eggplant flask, 1.336 g (12.1 mmol) of aminoguanidine hydrochloride, 6 mL of water, and 0.05 mL of 12 N hydrochloric acid were added and stirred at room temperature for 10 minutes, and 990 mg (14.7 mmol) of acrolein was then added thereto and the resultant was stirred with a magnetic stirrer at room temperature. After 1.5 hours of stirring, 20 mL of a saturated aqueous solution of sodium hydrogen carbonate was added to the reaction solution. A crystal precipitated was collected by filtration, washed with water, and then vacuum-dried at 50° C. for 24 hours to afford 402 mg (2.8 mmol) of a light yellow solid. The solid obtained was analyzed by using $^1$H-NMR, and confirmed to be allylideneaminoguanidine hemicarbonate ($^1$H-NMR (DMSO-d6, 500 MHz, δ; ppm)=5.3 (dd; 1H), 5.4 (dd; 1H), 5.4 (s; 2H), 5.9 (s; 2H), 6.4 (ddd; 1H), 7.7 (d; 1H)). The mole yield was 23%. The melting point was measured with the micro melting point measurement apparatus BY-1 (manufactured by YAZAWA Kagaku Co., Ltd.) to be 80° C. Elemental analysis was performed with the carbon/hydrogen/nitrogen simultaneous determination apparatus CHN coder MT-6 (manufactured by YANACO Co., Ltd.), and the result was as follows. Calc.: C, 37.76; H, 6.34; N, 39.14. Found: C, 37.35; H, 6.36; N, 38.52.

(Example A-8) Synthesis of 2-methylallylideneaminoguanidine carbonate (12)

(12)

To a 50 mL eggplant flask, 1.339 g (12.1 mmol) of aminoguanidine hydrochloride, 3 mL of water, and 0.025 mL of 12 N hydrochloric acid were added and stirred at room temperature for 10 minutes, and 1.03 g (14.6 mmol) of methacrolein was then added thereto and the resultant was stirred with a magnetic stirrer at room temperature. After 2 hours of stirring, 20 mL of a saturated aqueous solution of sodium hydrogen carbonate was added to the light yellow reaction solution. A crystal precipitated was collected by filtration, washed with water, and then vacuum-dried at 50° C. for 24 hours to afford 1.50 g (8.0 mmol) of a light yellow solid. The solid obtained was analyzed by using $^1$H-NMR, and confirmed to be 2-methylallylideneaminoguanidine carbonate ($^1$H-NMR (DMSO-d6, 500 MHz, δ; ppm)=1.9 (s; 3H), 5.1 (s; 1H), 5.2 (s; 1H), 5.3-5.8 (br), 7.7 (s; 1H)). The mole yield was 66%. The melting point was measured with the micro melting point measurement apparatus BY-1

(manufactured by YAZAWA Kagaku Co., Ltd.) to be 99 to 100° C. Elemental analysis was performed with the carbon/hydrogen/nitrogen simultaneous determination apparatus CHN coder MT-6 (manufactured by YANACO Co., Ltd.), and the result was as follows. Calc.: C, 38.29; H, 6.43; N, 29.77. Found: C, 38.83; H, 6.60; N, 30.80.

(Example A-9) Synthesis of 2-butenylideneaminoguanidine carbonate (13)

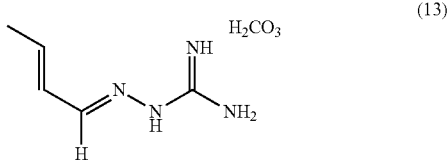

To a 50 mL eggplant flask, 1.337 g (12.1 mmol) of aminoguanidine hydrochloride, 2.2 mL of water, and 0.2 mL of 12 N hydrochloric acid were added and stirred at room temperature for 10 minutes, and 956 mg (13.6 mmol) of crotonaldehyde was then added thereto and the resultant was stirred with a magnetic stirrer at room temperature. After 1 hour of stirring, 20 mL of a saturated aqueous solution of sodium hydrogen carbonate was added to the reaction solution. A crystal precipitated was collected by filtration, washed with water, and then vacuum-dried at 50° C. for 20 hours to afford 1.23 g (6.5 mmol) of a white solid. The solid obtained was analyzed by using $^1$H-NMR, and confirmed to be 2-butenylideneaminoguanidine carbonate ($^1$H-NMR (DMSO-d6, 500 MHz, δ; ppm)=1.8 (dd; 3H), 5.2-5.7 (br), 5.9 (dq; 1H), 6.1 (m; 1H), 7.6 (d; 1H)). The mole yield was 54%. The melting point was measured with the micro melting point measurement apparatus BY-1 (manufactured by YAZAWA Kagaku Co., Ltd.) to be 124 to 125° C. Elemental analysis was performed with the carbon/hydrogen/nitrogen simultaneous determination apparatus CHN coder MT-6 (manufactured by YANACO Co., Ltd.), and the result was as follows. Calc.: C, 38.29; H, 6.43; N, 29.77. Found: C, 39.99; H, 6.79; N, 32.60.

Examples A-10 and 11

In 100% by mass of a natural rubber, 50% by mass of silica, 5% by mass of a silane coupling agent, 3% by mass of zinc oxide, 1% by mass of stearic acid, 1.75% by mass of sulfur, 1% by mass of a vulcanization accelerator (N-cyclohexyl-2-benzothiazolylsulfenamide), and 0.5% by mass of a vulcanization accelerator (diphenylguanidine) were blended and kneaded with a Labo Plastmill (manufactured by Toyo Seiki Seisaku-sho, Ltd.) to prepare a rubber composition A (Comparative Example A-1), which was vulcanized with a pressing machine (manufactured by KITAGAWA SEIKI Co., Ltd.) at 145° C. and 10 MPa for 25 to 37 minutes to obtain a vulcanized rubber composition. And then, 0.7% by mass of the compound in Example A-1 was further blended in a blend for the rubber composition A to prepare a rubber composition B (Test Example A-1) in the same manner.

Furthermore, 0.8% by mass of the compound in Example A-8 was further blended in a blend for the rubber composition A to prepare a rubber composition C (Test Example A-2) in the same manner. Also for each of the rubber compositions B and C, preparation was performed by kneading with a Labo Plastmill (manufactured by Toyo Seiki Seisaku-sho, Ltd.), and the rubber composition prepared was vulcanized with a pressing machine (manufactured by KITAGAWA SEIKI Co., Ltd.) at 145° C. and 10 MPa for 25 to 37 minutes to obtain a vulcanized rubber composition in the same manner as for the rubber composition A.

The components used are shown as follows.

Natural rubber: RSS #1

Silica: product name "Nipsil AQ" (BET specific surface area=207 m$^2$/g, manufactured by Tosoh Silica Corporation)

Silane coupling agent: bis(3-triethoxysilylpropyl) tetrasulfide (manufactured by Evonic Japan Co., Ltd.)

Zinc oxide (manufactured by Wako Pure Chemical Industries, Ltd.)

Stearic acid (manufactured by Wako Pure Chemical Industries, Ltd.)

Sulfur (manufactured by Hosoi Chemical Industry Co., Ltd., 250 µm)

Vulcanization accelerator (CBS): N-cyclohexyl-2-benzothiazolylsulfenamide (manufactured by Wako Pure Chemical Industries, Ltd.)

Vulcanization accelerator (DPG): diphenylguanidine (manufactured by Wako Pure Chemical Industries, Ltd.)

For the vulcanized rubber composition, Heat build-upheat build-up and tensile breaking strength were measured and evaluated by using the following methods.

(1) Heat Build-Up

The loss tangent (tan δ) of the vulcanized rubber composition was measured with a dynamic viscoelastometer (DMS6100 manufactured by Seiko Instruments Inc.) at a temperature of 50° C., a strain of 0.05%, and a frequency of 10 Hz, and each of the values for Test Example A-1 (rubber composition B) and Test Example A-2 (rubber composition C) was represented by an index number assuming the value for Comparative Example A-1 (rubber composition A) as 100. A smaller index number corresponds to lower tan δ, and indicates that the rubber composition has low loss properties.

(2) Tensile Breaking Strength

The vulcanized rubber composition was subjected to a tensile test to measure the tensile breaking strength in accordance with JIS K6251: 2010, and each of the values for Test Example A-1 (rubber composition B) and Test Example A-2 (rubber composition B) was represented by an index number assuming the value for Comparative Example A-1 (rubber composition A) as 100. A larger index number corresponds to a larger tensile breaking strength, and indicates that the fracture resistance is satisfactory.

The results were that the tan δ and the tensile breaking strength of the vulcanized rubber composition in Test Example A-1 (rubber composition B) were 80 and 111, respectively, and the tan δ and the tensile breaking strength of the vulcanized rubber composition in Test Example A-2 (rubber composition C) were 85 and 109, respectively, assuming the tan δ and the tensile breaking strength of the vulcanized rubber composition in Comparative Example A-1 (rubber composition A) as 100. From the results, it was at least found that the compounds in Example A-1 (see Test Example A-1, rubber composition B) and Example A-8 (see Test Example A-2, rubber composition C) are useful for enhancement of the low loss properties and breaking strength of a rubber.

Experiment B (Example B-1) Synthesis of 1,3-dimethylbutylideneaminoguanidine carbonate (3)

1,3-Dimethylbutylideneaminoguanidine carbonate synthesized in (Example A-1) was used.

(Example B-2) Synthesis of 3-phenylallylideneaminoguanidine (4)

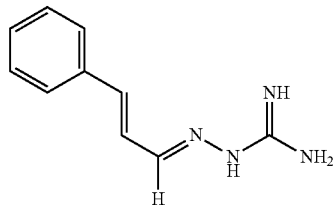

(4)

To a 50 mL eggplant flask, 1.332 g (12.0 mmol) of aminoguanidine hydrochloride, 6 mL of methanol, and 0.25 mL of 12 N hydrochloric acid were added and stirred at room temperature for 10 minutes, and 1.609 g (12.2 mmol) of cinnamaldehyde was then added thereto and the resultant was stirred with a magnetic stirrer at room temperature. After 2 hours of stirring, the reaction solution was added dropwise to 20 mL of a saturated aqueous solution of sodium hydrogen carbonate to precipitate a light yellow crystal, which was collected by filtration, washed with water, and then vacuum-dried at 50° C. for 24 hours to afford 2.213 g (11.8 mmol) of a light yellow solid. The solid obtained was analyzed by using $^1$H-NMR, and confirmed to be 3-phenylallylideneaminoguanidine ($^1$H-NMR (DMSO-d6, 500 MHz, δ; ppm)=5.5 (s; 2H), 5.7-5.8 (br; 2H), 6.7 (d; 1H), 6.9 (dd; 1H), 7.2 (dd; 1H), 7.3 (dd; 2H), 7.5 (d; 2H), 7.8 (d; 1H)). The mole yield was 98%. The melting point was measured with the micro melting point measurement apparatus BY-1 (manufactured by YAZAWA Kagaku Co., Ltd.) to be 190 to 192° C. Elemental analysis was performed with the carbon/hydrogen/nitrogen simultaneous determination apparatus CHN coder MT-6 (manufactured by YANACO Co., Ltd.), and the result was as follows. Calc.: C, 63.81; H, 6.43; N, 29.77. Found: C, 63.26; H, 6.45; N, 29.43.

(Example B-3) Synthesis of 2-methylallylideneaminoguanidine carbonate (5)

2-methylallylideneaminoguanidine carbonate synthesized in (Example A-8) was used.

(Example B-4) Synthesis of 1-methylethylideneaminoguanidine phosphate (6)

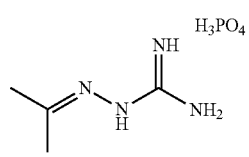

(6)

To a 50 mL eggplant flask, 8.13 g (60 mmol) of aminoguanidine carbonate (manufactured by Tokyo Chemical Industry Co., Ltd.) and 12 mL of water were added and 7.01 g (60 mmol) of 85% phosphoric acid was added dropwise thereto, and the resultant was stirred at room temperature for 30 minutes. Subsequently, 3.52 g (61 mmol) of acetone was added thereto, and the resultant was stirred with a magnetic stirrer at room temperature. After stirring, a white solid precipitated. After 3 hours of additional stirring at room temperature, the crystal was collected by filtration, and acetone was added to the filtrate obtained to further precipitate a white solid. The crystal obtained was washed with acetone, and then vacuum-dried at 35° C. for 20 hours to afford 11.27 g (53.1 mmol) of a white solid. The solid obtained was analyzed by using $^1$H-NMR, and confirmed to be 1-methylethylideneaminoguanidine phosphate ($^1$H-NMR (DMSO-d6, 500 MHz, δ; ppm)=1.9 (s; 1H), 2.0 (s; 1H), 7.4-8.2 (br)). The mole yield was 89%. The melting point was measured with the micro melting point measurement apparatus BY-1 (manufactured by YAZAWA Kagaku Co., Ltd.) to be 209 to 210° C. Elemental analysis was performed with the carbon/hydrogen/nitrogen simultaneous determination apparatus CHN coder MT-6 (manufactured by YANACO Co., Ltd.), and the result was as follows. Calc.: C, 22.65; H, 6.18; N, 26.41. Found: C, 22.03; H, 6.29; N, 25.97.

(Example B-5) Synthesis of 1-phenylethylideneaminoguanidine phosphate (7)

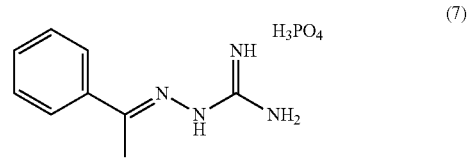

(7)

To a 50 mL eggplant flask, 13.62 g (100 mmol) of aminoguanidine carbonate and 42 mL of water were added and 12.35 g (107 mmol) of 85% phosphoric acid was added dropwise thereto. After 30 minutes of stirring at room temperature, 12.25 g (102 mmol) of acetophenone was added thereto, and the resultant was stirred with a magnetic stirrer at room temperature. As a result, a white solid precipitated. After 4 hours of stirring, the crystal precipitated was collected by filtration, washed with water, and then vacuum-dried at 35° C. for 24 hours to afford 24.67 g (90 mmol) of a white solid. The solid obtained was analyzed by using $^1$H-NMR, and confirmed to be 1-phenylethylideneaminoguanidine phosphate ($^1$H-NMR (DMSO-d6, 500 MHz, δ; ppm)=2.3 (s; 3H), 4.2-4.7 (br), 7.4 (m; 3H), 7.9 (m; 2H)). The mole yield was 90%. The melting point was measured with the micro melting point measurement apparatus BY-1 (manufactured by YAZAWA Kagaku Co., Ltd.) to be 235 to 236° C. Elemental analysis was performed with the carbon/hydrogen/nitrogen simultaneous determination apparatus CHN coder MT-6 (manufactured by YANACO Co., Ltd.), and the result was as follows. Calc.: C, 39.42; H, 5.51; N, 20.43. Found: C, 37.89; H, 5.57; N, 19.76.

Example B-6

In a Labo Plastmill (manufactured by Toyo Seiki Seisakusho, Ltd.) with the inside of the reactor heated to 30° C., 41.4 g of a natural rubber coagulate (RSS #1, manufactured by Kato Sansho Co., Ltd.) was placed and kneaded at a rotational frequency of 60 rpm, for 4 minutes with the lid closed and for 1 minute with the lid opened. When the temperature of the rubber increased to reach 80° C. due to shear heating, 0.290 g of 1,3-dimethylbutylideneaminoguanidine carbonate obtained in Synthesis of Example A-1 was placed therein, and the resultant was further kneaded for 3 minutes to obtain a modified rubber 1. Then, the temperature of the rubber had reached 85° C.

In 200 g of a 2:1 mixed solvent of acetone and methanol, 9.0 g of the modified rubber 1 was heated to reflux for 2 hours to extract unreacted 1,3-dimethylbutylideneaminoguanidine carbonate. After the solvent was distilled away under reduced pressure, the residue was subjected to quantitative analysis by using liquid chromatography, and the result showed that the quantity of unreacted 1,3-dimethylbutylideneaminoguanidine carbonate contained in the extract was 0.008 g, in other words, 87% of 1,3-dimethylbutylideneaminoguanidine carbonate added reacted with the natural rubber.

Thus, it was found that the amount of addition of aminoguanidine in the modified rubber 1 was 0.6% by mass, based on the amount of the solid rubber component of the natural rubber raw material.

Example B-7

In a Labo Plastmill with the inside of the reactor heated to 30° C., 41.4 g of a natural rubber coagulate (RSS #1) was placed and kneaded at a rotational frequency of 60 rpm, for 4 minutes with the lid closed and for 1 minute with the lid opened. When the temperature of the rubber increased to reach 80° C. due to shear heating, 0.290 g of 3-phenylallylideneaminoguanidine obtained in Synthesis of Example B-2 was placed therein, and the resultant was further kneaded for 3 minutes to obtain a modified rubber 2. Then, the temperature of the rubber had reached 85° C.

In 200 g of a 2:1 mixed solvent of acetone and methanol, 9.0 g of the modified rubber 2 was heated to reflux for 2 hours to extract unreacted 3-phenylallylideneaminoguanidine. After the solvent was distilled away under reduced pressure, the residue was subjected to quantitative analysis by using liquid chromatography, and the result showed that the quantity of unreacted 3-phenylallylideneaminoguanidine was 0.022 g, in other words, 65% of 3-phenylallylideneaminoguanidine contained in the extract added reacted with the natural rubber.

Thus, it was found that the amount of addition of aminoguanidine in the modified rubber 2 was 0.5% by mass, based on the amount of the solid rubber component of the natural rubber raw material.

Reference Example 1

In a Labo Plastmill with the inside of the reactor heated to 30° C., 41.4 g of a natural rubber coagulate (RSS #1) was placed and kneaded at a rotational frequency of 60 rpm, for 4 minutes with the lid closed and for 1 minute with the lid opened. After the temperature of the rubber reached 80° C. due to shear heating, the rubber was further kneaded for 3 minutes to obtain an unmodified rubber 1. Then, the temperature of the rubber had reached 85° C.

Examples B-8 and B-9, Comparative Example B-1

In accordance with a composition listed in Table 1, the modified rubber 1 or 2, or the unmodified rubber 1 was first kneaded with silica, a silane coupling agent, zinc oxide, and stearic acid with a Labo Plastmill at 140° C. for 5 minutes, and the resultant was then cooled to 55° C. Sulfur and a vulcanization accelerator were placed therein, and the resultant was kneaded at 90° C. for 3 minutes to prepare a rubber composition. Subsequently, the rubber composition was vulcanized with a pressing machine (manufactured by KITAGAWA SEIKI Co., Ltd.) at 145° C. and 10 MPa for 26 to 38 minutes to obtain a vulcanized rubber composition. The components used are shown below.

Examples B-10 to 14, Comparative Example B-2

In accordance with a composition listed in Table 2, a natural rubber coagulate, silica, a silane coupling agent, zinc oxide, stearic acid, and one of modifiers 1 to 5 were first kneaded together with a Labo Plastmill at 140° C. for 5 minutes, and the resultant was then cooled to 55° C. Sulfur and a vulcanization accelerator were placed therein, and the resultant was kneaded at 90° C. for 3 minutes to prepare a rubber composition. Subsequently, the rubber composition was vulcanized with a pressing machine (manufactured by KITAGAWA SEIKI Co., Ltd.) at 145° C. and 10 MPa for 25 to 37 minutes to obtain a vulcanized rubber composition. The components used are shown as follows.
Natural rubber: RSS #1
Silica: product name "Nipsil AQ" (BET specific surface area=207 m$^2$/g, manufactured by Tosoh Silica Corporation)
Silane coupling agent: bis(3-triethoxysilylpropyl) tetrasulfide (manufactured by Evonic Japan Co., Ltd.)
Zinc oxide (manufactured by Wako Pure Chemical Industries, Ltd.)
Stearic acid (manufactured by Wako Pure Chemical Industries, Ltd.)
Sulfur (manufactured by Hosoi Chemical Industry Co., Ltd., 250 μm)
Vulcanization accelerator (CBS): N-cyclohexyl-2-benzothiazolylsulfenamide (manufactured by Wako Pure Chemical Industries, Ltd.)
Vulcanization accelerator (DPG): diphenylguanidine (manufactured by Wako Pure Chemical Industries, Ltd.)
Modifier 1: 1,3-dimethylbutylideneaminoguanidine carbonate obtained in Example B-1
Modifier 2: 3-phenylallylideneaminoguanidine obtained in Example B-2
Modifier 3: 2-methylallylideneaminoguanidine carbonate obtained in Example B-3
Modifier 4: 1-methylethylideneaminoguanidine phosphate obtained in Example B-4
Modifier 5: 1-phenylethylideneaminoguanidine phosphate obtained in Example B-5

For the vulcanized rubber composition, heat build-up and tensile breaking strength were measured and evaluated by using the following methods. The results are shown in Tables 1 and 2.
(1) Heat Build-Up The loss tangent (tan δ) of the vulcanized rubber composition was measured with a dynamic viscoelastometer (DMS6100 manufactured by Seiko Instruments Inc.) at a temperature of 50° C., a strain of 0.05%, and a frequency of 10 Hz, and represented by an index number in Table 1 and Table 2, assuming the value for Comparative Example B-1 as 100 in Table 1 and assuming the value for Comparative Example B-2 as 100 in Table 2. A smaller index number corresponds to lower tan δ, and indicates that the rubber composition has low heat build-up.

(2) Tensile Breaking Strength

The vulcanized rubber composition was subjected to a tensile test to measure the tensile breaking strength in accordance with JIS K6251-2010, and represented by an index number, assuming the value for Comparative Example B-1 as 100 in Table 1 and assuming the value for Comparative Example B-2 as 100 in Table 2. A larger index number corresponds to a larger tensile breaking strength.

TABLE 1

|  | Example B-8 | Example B-9 | Comparative Example B-1 |
| --- | --- | --- | --- |
| Modified rubber 1 | 100 | — | — |
| Modified rubber 2 | — | 100 | — |
| Unmodified rubber 1 | — | — | 100 |
| Silica | 50 | 50 | 50 |
| Silane coupling agent | 5 | 5 | 5 |
| Zinc oxide | 3 | 3 | 3 |
| Stearic acid | 1 | 1 | 1 |
| Sulfur | 1.75 | 1.75 | 1.75 |
| Vulcanization accelerator (CBS) | 1 | 1 | 1 |
| Vulcanization accelerator (DPG) | 0.5 | 0.5 | 0.5 |
| Heat build-up | 76 | 71 | 100 |
| Tensile breaking strength | 118 | 121 | 100 |

In Table 1, each component of a formulation is in part by mass.

From Table 1, it was at least found that the rubber composition in each of Examples had better low heat build-up and larger tensile breaking strength than a rubber composition obtained from a mixture with a diene rubber not modified with an alkylidene aminoguanidine salt or alkylidene aminoguanidine.

TABLE 2

|  | Example B-10 | Example B-11 | Example B-12 | Example B-13 | Example B-14 | Comparative Example B-2 |
| --- | --- | --- | --- | --- | --- | --- |
| Natural rubber | 100 | 100 | 100 | 100 | 100 | 100 |
| Silica | 50 | 50 | 50 | 50 | 50 | 50 |
| Silane coupling agent | 5 | 5 | 5 | 5 | 5 | 5 |
| Zinc oxide | 3 | 3 | 3 | 3 | 3 | 3 |
| Stearic acid | 1 | 1 | 1 | 1 | 1 | 1 |
| Sulfur | 1.75 | 1.75 | 1.75 | 1.75 | 1.75 | 1.75 |
| Vulcanization accelerator (CBS) | 1 | 1 | 1 | 1 | 1 | 1 |
| Vulcanization accelerator (DPG) | 0.5 | 0.5 | 0.5 | 0.5 | 0.5 | 0.5 |
| Modifier 1 | 0.7 | — | — | — | — | — |
| Modifier 2 | — | 0.7 | — | — | — | — |
| Modifier 3 | — | — | 0.8 | — | — | — |
| Modifier 4 | — | — | — | 1 | — | — |
| Modifier 5 | — | — | — | — | 1 | — |
| Heat build-up | 80 | 87 | 85 | 91 | 88 | 100 |
| Tensile breaking strength | 111 | 108 | 109 | 102 | 105 | 100 |

In Table 2, each component of a formulation is in part by mass.

From Table 2, it was at least found that the rubber composition in each of Examples had better low heat build-up and larger tensile breaking strength than a rubber composition obtained from a mixture with no alkylidene aminoguanidine salt or alkylidene aminoguanidine added.

The compound, modified rubber for a tire, and rubber composition for a tire according to the present invention can be used as a material for various members of a tire including a tread.

The invention claimed is:

1. A modified rubber for a tire (A), which is obtained by reacting a natural rubber and/or a synthetic rubber with a compound represented by formula (1) or formula (2):

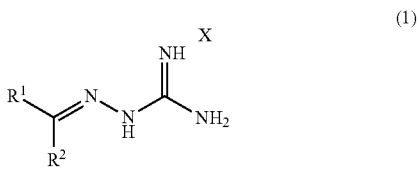

wherein X is an acid to form a salt with a guanidine site; and $R^1$ and $R^2$ are each independently any selected from the group consisting of a hydrogen atom, a $C_{1-18}$ alkyl group, a cycloalkyl group, an aryl group, an alkylaryl group, and an alkenyl group, each of the groups optionally having one or more substituents each containing a sulfur atom, a nitrogen atom, or an oxygen atom, (2)

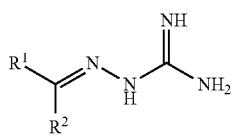

wherein R¹ and R² are each independently any selected from the group consisting of a hydrogen atom, a $C_{1-18}$ alkyl group, a cycloalkyl group, an aryl group, an alkylaryl group, and an alkenyl group, each of the groups optionally having one or more substituents each containing a sulfur atom, a nitrogen atom, or an oxygen atom.

2. The modified rubber for a tire (A) according to claim 1, wherein the compound is obtained by reacting an aminoguanidine salt represented by formula (3) with a carbonyl compound represented by formula (4):

(3)

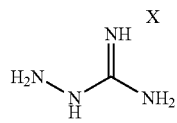

wherein X is an acid to form a salt with a guanidine site in the formula (3), (4)

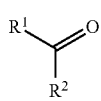

wherein R¹ and R² are each independently any selected from the group consisting of a hydrogen atom, a $C_{1-18}$ alkyl group, a cycloalkyl group, an aryl group, an alkylaryl group, and an alkenyl group, each of the groups optionally having one or more substituents each containing a sulfur atom, a nitrogen atom, or an oxygen atom.

3. The modified rubber for a tire (A) according to claim 1, wherein R¹ and R² in the formula (1) or the formula (2) are each independently any selected from the group consisting of a $C_{1-5}$ alkyl group and a hydrogen atom.

4. The modified rubber for a tire (A) according to claim 1, wherein the compound has a melting point of 50 to 150° C.

5. The modified rubber for a tire (A) according to claim 1, wherein the compound is represented by any of formulas (5) to (13):

(5)

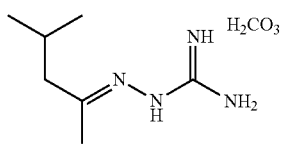

(6)

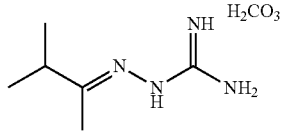

(7)

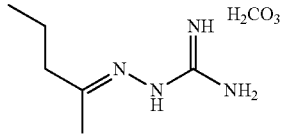

(8)

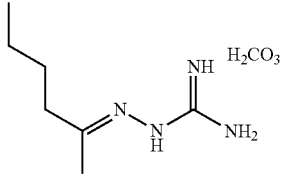

(9)

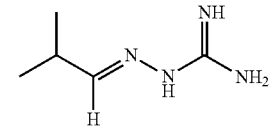

(10)

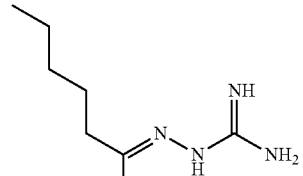

(11)

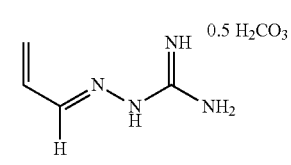

(12)

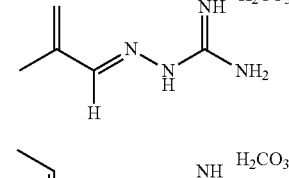

(13)

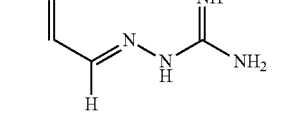

6. The modified rubber for a tire (A) according to claim 1, which is obtained by mixing the natural rubber and/or the synthetic rubber with the compound represented by the formula (1) or the formula (2) to modify the resulting mixture in the range of 20 to 180° C.

7. The modified rubber for a tire (A) according to claim 1, wherein the compound represented by the formula (1) or the formula (2) is used at 0.01 to 10% by mass, based on an amount of the natural rubber and/or the synthetic rubber.

8. A rubber composition for a tire comprising: the modified rubber for a tire (A) according to claim 1; a filler comprising an inorganic filler (B); and a silane coupling agent (C).

9. The rubber composition for the tire according to claim 8, wherein the inorganic filler (B) is silica.

10. The rubber composition for the tire according to claim 8, wherein the filler comprises carbon black.

11. The rubber composition for the tire according to claim 8 comprising the modified rubber for a tire (A), wherein the rubber composition is obtained by mixing the compound represented by the formula (1) or the formula (2), a natural rubber and/or a synthetic rubber, a filler containing an inorganic filler (B), and a silane coupling agent (C) together.

12. The rubber composition for the tire according to claim 11, wherein a temperature in mixing is in a range of 20 to 180° C.

13. The rubber composition for the tire according to claim 11, wherein a content of the compound represented by the formula (1) or the formula (2) is 0.01 to 10% by mass, based on an amount of the natural rubber and/or the synthetic rubber.

14. A tire for use in a tread of a tire member, comprising the rubber composition for a tire according to claim 8.

* * * * *